US008178319B2

(12) United States Patent
Pahlsson et al.

(10) Patent No.: US 8,178,319 B2
(45) Date of Patent: May 15, 2012

(54) PEPTIDES AND USES THEREOF

(76) Inventors: Peter Pahlsson, Linkoping (SE); Ingvar Ryden, Kalmar (SE)

( * ) Notice: Subject to any disclaimer, the term of this patent is extended or adjusted under 35 U.S.C. 154(b) by 0 days.

(21) Appl. No.: 12/991,493

(22) PCT Filed: May 8, 2009

(86) PCT No.: PCT/SE2009/050505
§ 371 (c)(1),
(2), (4) Date: Nov. 8, 2010

(87) PCT Pub. No.: WO2009/136859
PCT Pub. Date: Nov. 12, 2009

(65) Prior Publication Data
US 2011/0065148 A1    Mar. 17, 2011

(30) Foreign Application Priority Data

May 8, 2008    (SE) ...................................... 0801032

(51) Int. Cl.
C12P 21/06    (2006.01)
C07K 14/00    (2006.01)
G01N 33/48    (2006.01)
C07H 21/04    (2006.01)

(52) U.S. Cl. ................ 435/69.1; 435/252.33; 435/320.1; 436/63; 436/64; 436/86; 530/324; 530/350; 536/23.1

(58) Field of Classification Search .......................... None
See application file for complete search history.

(56) References Cited

U.S. PATENT DOCUMENTS 6,054,304 A * 4/2000 Taniguchi et al. ............ 435/193
2006/0251580 A1 11/2006 Keppler et al.

FOREIGN PATENT DOCUMENTS
WO   WO 98/55869 A1   12/1998

OTHER PUBLICATIONS

Garber et al. Specificity of the fucose-binding lectin of *Pseudomonas aeruginosa*. FEMS Microbiol. Lett. (1987) 48, 331-334.*
Amano, et al., "Production of Functional Lectin in Pichia Pastoris Directed by Cloned cDNA from *Aleuria aurantia*", Biosci. Biotechnol. Biochem., 67 (10), pp. 2277-2279 (2003).
Beppu, et al., "Photoaffinity Labeling of Concanavalin A Preparation of a Concanavalin A Derivative with Reduced Valence", J. Biochem., 78, pp. 1013-1019 (1975).
Beppu, et al., "Preparation of Monovalent Succinyl-concanavalin A and its Mitogenic Activity", J. Biochem., 79, pp. 1113-1117 (1976).
Debray, et al., "*Aleuria aurantia* Agglutinin. A New Isolation Procedure and Further Study of its Specificity Towards Various Glyco-Peptides and Oligosaccharides", Carbohydrate Research, 185, pp. 15-26 (1989).
Espinosa, et al., "NMR Investigations of Protein-Carbohydrate Interactions Binding Studies and Refined Three-Dimensional Solution Structure of the Complex Between the B Domain of Wheat Germ Agglutinin and N, N', N"-triacetylchitotriose", Eur. J. Biochem., 267, pp. 3965-3978 (2000).
Fraser, et al., "Monovalent Derivatives of Concanavalin A", Proc. Nat. Acad. Sci. Biochemistry, vol. 73, No. 3, pp. 790-794 (1976).
Fujihashi, et al., "Crystal Structure of Fucose-Specific Lectin from *Aleuria aurantia* Binding Ligands at Three of its Five Sugar Recognition Sites", Biochemistry, vol. 42, No. 38, pp. 11093-11099 (2003).
Fukumori, et al., "Cloning and Expression of a Functional Fucose-Specific Lectin from an Orange Peel Mushroom, *Aleuria aurantia*", FEBS 07254, vol. 250, No. 2, pp. 153-156 (1989).
Gunther, et al., "Concanavalin A Derivatives with Altered Biological Activities", Proc. Nat. Acad. Sci. USA, vol. 70, No. 4, pp. 1012-1016 (1973).
Hashimoto, et al., "alpha1-Acid Glycoprotein Fucosylation as a Marker of Carcinoma Progression and Prognosis", Cancer, vol. 101, No. 12, pp. 2825-2836 (2004).
Imberty, et al., "Structural Basis of High-Affinity Glycan Recognition by Bacterial and Fungal Lectins", Current Opinion in Structural Biology, 15, pp. 525-534 (2005).
Kaku, et al., "Monomeric, Monovalent Derivative of *Maackia amurensis* Leukoagglutinin", The Journal of Biological Chemistry, vol. 268, No. 18, pp. 13237-13241 (1993).
Kaku, et al., "Preparation of a Stable Subunit of Japanese Elderberry (*Sambucus sieboldiana*) Bark Lectin and its Application for the Study of Cell Surface Carbohydrates by Flow Cytometry", FEBS, vol. 306, No. 2,3, pp. 176-180 (1992).
Kochibe, et al., "Purification and Properties of a Novel Fucose-Specific Hemagglutinin of *Aleuria aurantia*", Biochemistry, 19, pp. 2841-2846 (1980).
Kostlanova, et al., "The Fucose-Binding Lectin from *Ralstonia solanacearum*", the Journal of Biological Chemistry, Vo.. 280, No. 30, pp. 27839-27849 (2005).
Kurokawa, et al., "Purification and Characterization of a Lectin from *Wistaria floribunda* Seeds", The Journal of Biological Chemistry, vol. 251, No. 18, pp. 5686-5693 (1976).
Liljeblad, et al., "Analysis of Glycoproteins in Cell Culture Supernatants Using a Lectin Immunosensor Technique", Biosensors and Bioelectronics, vol. 17, Issue 10, pp. 883-891 (2002).
Listinsky, et al., "A Potentially Critical Molecule in Pathologic Processes Including Neoplasia", Am. J. Clin. Pathol., 110, pp. 425-440 (1998).
Nagata, et al., "Crystallization and Characterization of a Lectin Obtained from a Mushroom, *Aleuria aurantia*", Biochemica et Biophysica Acta, 1076, pp. 187-190 (1991).
Olausson, et al., "Detection of a High Affinity Binding Site in Recombinant *Aleuria aurantia* Lectin", Glycoconjugate J. 25, pp. 753-762 (2008).
Ozeki, et al., "Developmental Expression of D-Galactoside-Binding Lectin in Sea Urchin (*Anthocidaris crassispina*) Eggs", Experimental Cell Research 216, pp. 318-324 (1995).
Rudiger, et al., "Plant Lectins: Occurrence, Biochemistry, Functions and Applications", Glycoconjugate Journal 18, pp. 589-613 (2001).

(Continued)

*Primary Examiner* — Nashaat Nashed
(74) *Attorney, Agent, or Firm* — Young & Thompson

(57) ABSTRACT

The present invention relates to monovalent fucose-binding peptides. The peptides may be recombinantly produced or chemically synthesized. Preferably the peptides are derived from a lectin, in particular *Aleuria aurantia* lectin. Furthermore the invention relates to methods for producing the peptides, assays using the peptides for diagnosis of disorders, as well as methods using the peptides for separation and detection of fucose-containing compounds.

17 Claims, 6 Drawing Sheets

OTHER PUBLICATIONS

Figure 3:
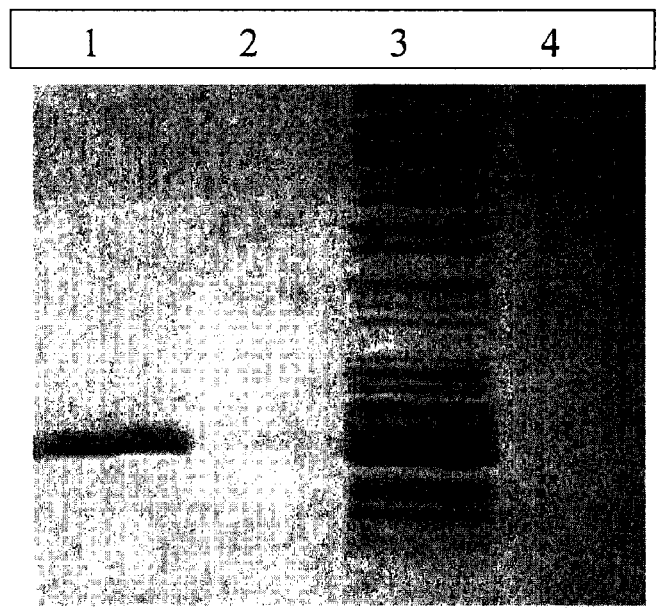

Ryden, et al., "Lectin ELISA for Analysis of alpha1-Acid Glycoprotein Fucosylation in the Acute Phase Response", Clinical Chemistry 45, No. 11, pp. 2010-2012 (1999).

Ryden, et al., "Diagnostic Accuracy of alpha1-Acid Glycoprotein Fucosylation for Liver Cirrhosis in Patients Undergoing Hepatic Biopsy", Clinical Chemistry 48:12, pp. 2195-2201 (2002).

Ryden, et al., "Fucosylation of alpha1-acid Glycoprotein (orosomucoid) Compared with Traditional Biochemical Markers of Inflammation in Recent Onset Rheumatoid Arthritis", Clinica Chimica Acta 317, pp. 221-229 (2002).

Tateno, et al., "Cloning, Expression in *Escherichia coli* and Characterization of the Recombinant Neu5Acα2, 6Galβ1, 4GlcNAc-specific high-affinity Lectin and its Mutants from the Mushroom Polyporus Squamosus", Biochem. J. 382, pp. 667-675 (2004).

Wands, et al., "Mechanism of Human Lymphocyte Stimulation by Concanavalin A: Role of Valence and Surface Binding Sites", Proc. Natl. Acad. Sci. USA, vol. 73, No. 6, pp. 2118-2122 (1976).

Wimmerova, et al., "Crystal Structure of Fungal Lectin", the Journal of Biological Chemistry, vol. 278, No. 29, pp. 27059-27067 (2003).

Yamashita, et al., "Fractionation of L-Fucose-containing Oligosaccharides on Immobilized *Aleuria aurantia* Lectin", The Journal of Biological Chemistry, vol. 260, No. 8, pp. 4688-4693 (1985).

International Search Report in connection with PCT/SE2009/050505 mailed Jul. 9, 2009.

Liljeblad et al: "A Lectin Immunosensor Technique for Determination of α1-Acid Glycoprotein Fucosylation", Analytical Biochemistry, 2001, vol. 288, pp. 216-224, XP002399205.

\* cited by examiner

Figure 1

```
         10          20         30          40         50         60
GSSHHHHHHS SGLVPRGSHM SQNVIGEAKL FSPLAAVTWK SAQGIQIRVY CVNKDNILSE 70         80          90        100         110        120
FVYDGSKWIT GQLGSVGVKV GSNSKLAALQ WGGSESAPPN IRVYYQKSNG SGSSIHEYVW

130
SGKWTAGASF G
```

Figure 2

*ATGGGCAGCAGCCATCATCATCATCATCACAGCAGCGGCCCTGGTGCCGCGCGGCAGCCATATGAGCCAGAATGTAATCGGCGAAGC*
*AAGCTTTTTCGCCACTGGCTGCTGTCACGTTGCTCAGGGCATACAGATCCGTGTTTACTGCGTCAATAAGG*
*ATAACATCCTCTCGAATTTGTTGTATGACGGTTCGAAGTGGATCGGGCAGTCGGGCGTCAAGGTGGGC*
*TCCAATTCGAAGCTTGCTGCGCTTCAGTGGGGGATCTCAGTGAGAGCGCCCCAAACATCCGAGTTACTACCAGAAGAG*
*CAACGGTAGTGGGAGCTCAATGTCTGGTCGGGCAAATGGACGGCTGGCGCAAGCTTTGGGTAA*

Figure 4
A
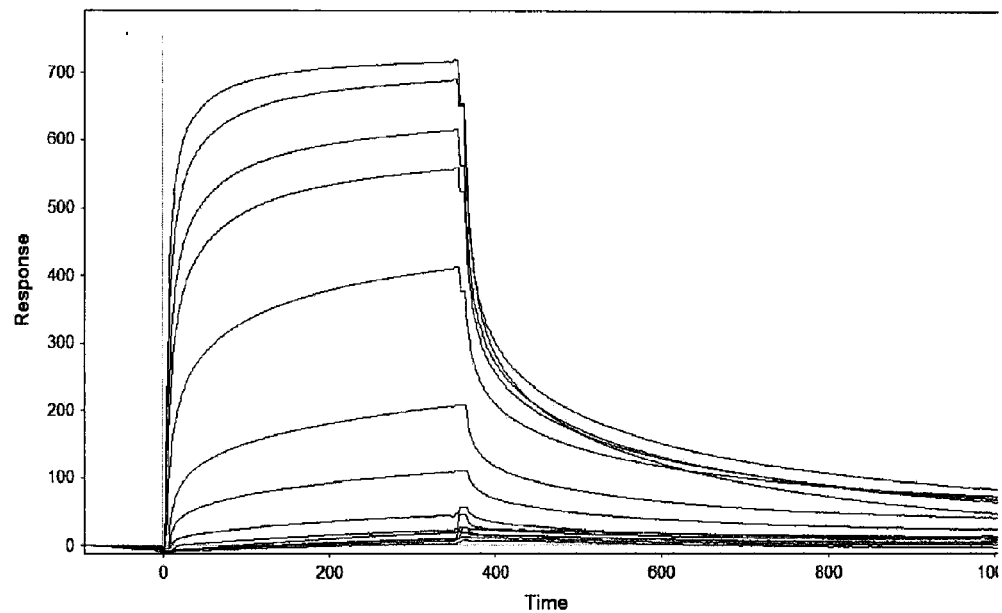
B
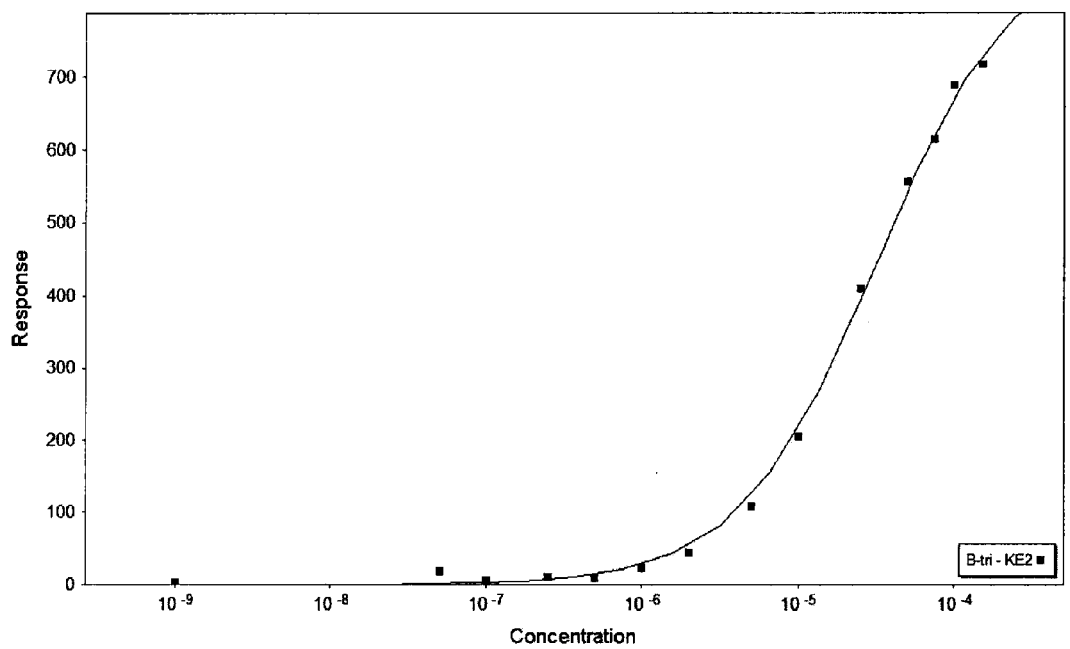

Figure 6

| Trivial name (abbreviated) | Oligosaccharide structure |
|---|---|
| LNT | Galβ1-3GlcNAcβ1-3Galβ1-4Glc |
| LNnF I | Fucα1-2Galβ1-4GlcNAcβ1-3Galβ1-4Glc |
| LNF II | Galβ1-3GlcNAcβ1-3Galβ1-4Glc<br>　　　　　4<br>　　　　　\|<br>　　　　Fucα1 |
| LNF III | Galβ1-4GlcNAcβ1-3Galβ1-4Glc<br>　　　　3<br>　　　　\|<br>　　　Fucα1 |
| B-tri | Fucα1-2Galβ<br>　　　　3<br>　　　　\|<br>　　　Galα1 |
| SLex | Neu5Acα2-3Galβ1-4GlcNAcβ1-3Galβ1-4Glc<br>　　　　　　　3<br>　　　　　　　\|<br>　　　　　　Fucα1 |
| SLea | Neu5Acα2-3Galβ1-3GlcNAcβ1-3Galβ1-4Glc<br>　　　　　　　4<br>　　　　　　　\|<br>　　　　　　Fucα1 |

SEQUENCE LISTING

<160> NUMBER OF SEQ ID NOS: 18

<210> SEQ ID NO 1
<211> LENGTH: 279
<212> TYPE: DNA
<213> ORGANISM: Aleuria aurantia
<220> FEATURE:
<221> NAME/KEY: CDS
<222> LOCATION: (1)..(279)
<223> OTHER INFORMATION: Mono-F1

<400> SEQUENCE: 1

```
tcg aaa att gca gcc atc tct tgg gct gcc acc ggc ggc cgc cag caa      48
Ser Lys Ile Ala Ala Ile Ser Trp Ala Ala Thr Gly Gly Arg Gln Gln
1               5                   10                  15 cgc gtc tac ttc caa gac ctt aat ggc aag atc cgc gag gct cag cgc      96
Arg Val Tyr Phe Gln Asp Leu Asn Gly Lys Ile Arg Glu Ala Gln Arg
            20                  25                  30 ggg gga gac aat cca tgg acc ggc ggg tcg agc cag aat gta atc ggc     144
Gly Gly Asp Asn Pro Trp Thr Gly Gly Ser Ser Gln Asn Val Ile Gly
        35                  40                  45 gaa gca aag ctt ttt tcg cca ctg gct gct gtc acg tgg aaa agt gct     192
Glu Ala Lys Leu Phe Ser Pro Leu Ala Ala Val Thr Trp Lys Ser Ala
    50                  55                  60 cag ggc ata cag atc cgt gtt tac tgc gtc aat aag gat aac atc ctc     240
Gln Gly Ile Gln Ile Arg Val Tyr Cys Val Asn Lys Asp Asn Ile Leu
65                  70                  75                  80 tcc gaa ttt gtg tat gac ggt tcg aag tgg atc acc gga                 279
Ser Glu Phe Val Tyr Asp Gly Ser Lys Trp Ile Thr Gly
                85                  90
```

<210> SEQ ID NO 2
<211> LENGTH: 93
<212> TYPE: PRT
<213> ORGANISM: Aleuria aurantia

<400> SEQUENCE: 2

```
Ser Lys Ile Ala Ala Ile Ser Trp Ala Ala Thr Gly Gly Arg Gln Gln
1               5                   10                  15

Arg Val Tyr Phe Gln Asp Leu Asn Gly Lys Ile Arg Glu Ala Gln Arg
            20                  25                  30

Gly Gly Asp Asn Pro Trp Thr Gly Gly Ser Ser Gln Asn Val Ile Gly
        35                  40                  45

Glu Ala Lys Leu Phe Ser Pro Leu Ala Ala Val Thr Trp Lys Ser Ala
    50                  55                  60

Gln Gly Ile Gln Ile Arg Val Tyr Cys Val Asn Lys Asp Asn Ile Leu
65                  70                  75                  80

Ser Glu Phe Val Tyr Asp Gly Ser Lys Trp Ile Thr Gly
                85                  90
```

<210> SEQ ID NO 3
<211> LENGTH: 333
<212> TYPE: DNA
<213> ORGANISM: Aleuria aurantia
<220> FEATURE:
<221> NAME/KEY: CDS
<222> LOCATION: (1)..(333)
<223> OTHER INFORMATION: Mono-F2

```
<400> SEQUENCE: 3 agc cag aat gta atc ggc gaa gca aag ctt ttt tcg cca ctg gct gct    48
Ser Gln Asn Val Ile Gly Glu Ala Lys Leu Phe Ser Pro Leu Ala Ala
1               5                   10                  15 gtc acg tgg aaa agt gct cag ggc ata cag atc cgt gtt tac tgc gtc    96
Val Thr Trp Lys Ser Ala Gln Gly Ile Gln Ile Arg Val Tyr Cys Val
                20                  25                  30 aat aag gat aac atc ctc tcc gaa ttt gtg tat gac ggt tcg aag tgg    144
Asn Lys Asp Asn Ile Leu Ser Glu Phe Val Tyr Asp Gly Ser Lys Trp
            35                  40                  45 atc acc gga cag ctg ggc agt gtc ggc gtc aag gtg ggc tcc aat tcg    192
Ile Thr Gly Gln Leu Gly Ser Val Gly Val Lys Val Gly Ser Asn Ser
        50                  55                  60 aag ctt gct gcg ctt cag tgg ggc gga tct gag agc gcc ccc cca aac    240
Lys Leu Ala Ala Leu Gln Trp Gly Gly Ser Glu Ser Ala Pro Pro Asn
65                  70                  75                  80 atc cga gtt tac tac cag aag agc aac ggt agt ggg agc tca atc cac    288
Ile Arg Val Tyr Tyr Gln Lys Ser Asn Gly Ser Gly Ser Ser Ile His
                85                  90                  95 gag tat gtc tgg tcg ggc aaa tgg acg gct ggc gca agc ttt ggg        333
Glu Tyr Val Trp Ser Gly Lys Trp Thr Ala Gly Ala Ser Phe Gly
                100                 105                 110

<210> SEQ ID NO 4
<211> LENGTH: 111
<212> TYPE: PRT
<213> ORGANISM: Aleuria aurantia

<400> SEQUENCE: 4

Ser Gln Asn Val Ile Gly Glu Ala Lys Leu Phe Ser Pro Leu Ala Ala
1               5                   10                  15

Val Thr Trp Lys Ser Ala Gln Gly Ile Gln Ile Arg Val Tyr Cys Val
                20                  25                  30

Asn Lys Asp Asn Ile Leu Ser Glu Phe Val Tyr Asp Gly Ser Lys Trp
            35                  40                  45

Ile Thr Gly Gln Leu Gly Ser Val Gly Val Lys Val Gly Ser Asn Ser
        50                  55                  60

Lys Leu Ala Ala Leu Gln Trp Gly Gly Ser Glu Ser Ala Pro Pro Asn
65                  70                  75                  80

Ile Arg Val Tyr Tyr Gln Lys Ser Asn Gly Ser Gly Ser Ser Ile His
                85                  90                  95

Glu Tyr Val Trp Ser Gly Lys Trp Thr Ala Gly Ala Ser Phe Gly
                100                 105                 110

<210> SEQ ID NO 5
<211> LENGTH: 264
<212> TYPE: DNA
<213> ORGANISM: Aleuria aurantia
<220> FEATURE:
<221> NAME/KEY: CDS
<222> LOCATION: (1)..(264)
<223> OTHER INFORMATION: Mono-F3

<400> SEQUENCE: 5 gct gcg ctt cag tgg ggc gga tct gag agc gcc ccc cca aac atc cga    48
Ala Ala Leu Gln Trp Gly Gly Ser Glu Ser Ala Pro Pro Asn Ile Arg
1               5                   10                  15 gtt tac tac cag aag agc aac ggt agt ggg agc tca atc cac gag tat    96
Val Tyr Tyr Gln Lys Ser Asn Gly Ser Gly Ser Ser Ile His Glu Tyr
                20                  25                  30
```

```
gtc tgg tcg ggc aaa tgg acg gct ggc gca agc ttt ggg tca acg gtg      144
Val Trp Ser Gly Lys Trp Thr Ala Gly Ala Ser Phe Gly Ser Thr Val
        35                  40                  45 cca gga acg ggt atc gga gcc acc gcc atc ggg cca ggt cgc ctg agg      192
Pro Gly Thr Gly Ile Gly Ala Thr Ala Ile Gly Pro Gly Arg Leu Arg
 50                  55                  60 atc tac tac cag gct act gac aac aag atc cgt gag cac tgt tgg gac      240
Ile Tyr Tyr Gln Ala Thr Asp Asn Lys Ile Arg Glu His Cys Trp Asp
 65                  70                  75                  80 tcc aac agt tgg tac gtg ggg ggg                                      264
Ser Asn Ser Trp Tyr Val Gly Gly
                     85

<210> SEQ ID NO 6
<211> LENGTH: 88
<212> TYPE: PRT
<213> ORGANISM: Aleuria aurantia

<400> SEQUENCE: 6

Ala Ala Leu Gln Trp Gly Gly Ser Glu Ser Ala Pro Pro Asn Ile Arg
 1               5                  10                  15

Val Tyr Tyr Gln Lys Ser Asn Gly Ser Gly Ser Ser Ile His Glu Tyr
             20                  25                  30

Val Trp Ser Gly Lys Trp Thr Ala Gly Ala Ser Phe Gly Ser Thr Val
         35                  40                  45

Pro Gly Thr Gly Ile Gly Ala Thr Ala Ile Gly Pro Gly Arg Leu Arg
 50                  55                  60

Ile Tyr Tyr Gln Ala Thr Asp Asn Lys Ile Arg Glu His Cys Trp Asp
 65                  70                  75                  80

Ser Asn Ser Trp Tyr Val Gly Gly
                     85

<210> SEQ ID NO 7
<211> LENGTH: 255
<212> TYPE: DNA
<213> ORGANISM: Aleuria aurantia
<220> FEATURE:
<221> NAME/KEY: CDS
<222> LOCATION: (1)..(255)
<223> OTHER INFORMATION: Mono-F4

<400> SEQUENCE: 7 gga acg ggt atc gga gcc acc gcc atc ggg cca ggt cgc ctg agg atc       48
Gly Thr Gly Ile Gly Ala Thr Ala Ile Gly Pro Gly Arg Leu Arg Ile
 1               5                  10                  15 tac tac cag gct act gac aac aag atc cgt gag cac tgt tgg gac tcc       96
Tyr Tyr Gln Ala Thr Asp Asn Lys Ile Arg Glu His Cys Trp Asp Ser
             20                  25                  30 aac agt tgg tac gtg ggg ggg ttc tcg gcc agc gct tcc gcc ggc gtc      144
Asn Ser Trp Tyr Val Gly Gly Phe Ser Ala Ser Ala Ser Ala Gly Val
         35                  40                  45 tcc atc gcg gcg att tct tgg ggc agt aca ccc aac atc cgg gtc tac      192
Ser Ile Ala Ala Ile Ser Trp Gly Ser Thr Pro Asn Ile Arg Val Tyr
 50                  55                  60 tgg cag aaa ggt agg gag gaa ttg tac gag gct gcc tat ggc ggt tca      240
Trp Gln Lys Gly Arg Glu Glu Leu Tyr Glu Ala Ala Tyr Gly Gly Ser
 65                  70                  75                  80 tgg aac act cct ggt                                                  255
Trp Asn Thr Pro Gly
                 85
```

-continued

```
<210> SEQ ID NO 8
<211> LENGTH: 85
<212> TYPE: PRT
<213> ORGANISM: Aleuria aurantia

<400> SEQUENCE: 8

Gly Thr Gly Ile Gly Ala Thr Ala Ile Gly Pro Gly Arg Leu Arg Ile
1               5                   10                  15

Tyr Tyr Gln Ala Thr Asp Asn Lys Ile Arg Glu His Cys Trp Asp Ser
            20                  25                  30

Asn Ser Trp Tyr Val Gly Gly Phe Ser Ala Ser Ala Ser Ala Gly Val
        35                  40                  45

Ser Ile Ala Ala Ile Ser Trp Gly Ser Thr Pro Asn Ile Arg Val Tyr
    50                  55                  60

Trp Gln Lys Gly Arg Glu Glu Leu Tyr Glu Ala Ala Tyr Gly Gly Ser
65                  70                  75                  80

Trp Asn Thr Pro Gly
                85

<210> SEQ ID NO 9
<211> LENGTH: 267
<212> TYPE: DNA
<213> ORGANISM: Aleuria aurantia
<220> FEATURE:
<221> NAME/KEY: CDS
<222> LOCATION: (1)..(267)
<223> OTHER INFORMATION: Mono-F5

<400> SEQUENCE: 9 tcc atc gcg gcg att tct tgg ggc agt aca ccc aac atc cgg gtc tac    48
Ser Ile Ala Ala Ile Ser Trp Gly Ser Thr Pro Asn Ile Arg Val Tyr
1               5                   10                  15 tgg cag aaa ggt agg gag gaa ttg tac gag gct gcc tat ggc ggt tca    96
Trp Gln Lys Gly Arg Glu Glu Leu Tyr Glu Ala Ala Tyr Gly Gly Ser
            20                  25                  30 tgg aac act cct ggt cag atc aag gac gca tcc agg cct acg ccc tcg   144
Trp Asn Thr Pro Gly Gln Ile Lys Asp Ala Ser Arg Pro Thr Pro Ser
        35                  40                  45 ttg cca gac acc ttt att gct gcg aac tcc tcg ggg aac atc gac atc   192
Leu Pro Asp Thr Phe Ile Ala Ala Asn Ser Ser Gly Asn Ile Asp Ile
    50                  55                  60 tct gtg ttc ttc caa gct agc ggc gtc tcc ttg cag cag tgg caa tgg   240
Ser Val Phe Phe Gln Ala Ser Gly Val Ser Leu Gln Gln Trp Gln Trp
65                  70                  75                  80 atc tcc ggc aag ggc tgg tcc atc ggc                               267
Ile Ser Gly Lys Gly Trp Ser Ile Gly
                85

<210> SEQ ID NO 10
<211> LENGTH: 89
<212> TYPE: PRT
<213> ORGANISM: Aleuria aurantia

<400> SEQUENCE: 10

Ser Ile Ala Ala Ile Ser Trp Gly Ser Thr Pro Asn Ile Arg Val Tyr
1               5                   10                  15

Trp Gln Lys Gly Arg Glu Glu Leu Tyr Glu Ala Ala Tyr Gly Gly Ser
            20                  25                  30

Trp Asn Thr Pro Gly Gln Ile Lys Asp Ala Ser Arg Pro Thr Pro Ser
        35                  40                  45

Leu Pro Asp Thr Phe Ile Ala Ala Asn Ser Ser Gly Asn Ile Asp Ile
    50                  55                  60
```

```
Ser Val Phe Phe Gln Ala Ser Gly Val Ser Leu Gln Gln Trp Gln Trp
 65                  70                  75                  80

Ile Ser Gly Lys Gly Trp Ser Ile Gly
                 85

<210> SEQ ID NO 11
<211> LENGTH: 46
<212> TYPE: DNA
<213> ORGANISM: Artificial Sequence
<220> FEATURE:
<223> OTHER INFORMATION: Synthetic Primer - NdeI mut forward

<400> SEQUENCE: 11
ggagacaatc catggaccgg ccatatgagc cagaatgtaa tcggcg             46

<210> SEQ ID NO 12
<211> LENGTH: 45
<212> TYPE: DNA
<213> ORGANISM: Artificial Sequence
<220> FEATURE:
<223> OTHER INFORMATION: Synthetic Primer - NdeI mut reverse

<400> SEQUENCE: 12
cgccgattac attctggctc atatggccgg tccatggatt gtctc              45

<210> SEQ ID NO 13
<211> LENGTH: 31
<212> TYPE: DNA
<213> ORGANISM: Artificial Sequence
<220> FEATURE:
<223> OTHER INFORMATION: Synthetic Primer - STOP mut forward

<400> SEQUENCE: 13
gcgcaagctt tgggtaaacg gtgccaggaa c                             31

<210> SEQ ID NO 14
<211> LENGTH: 31
<212> TYPE: DNA
<213> ORGANISM: Artificial Sequence
<220> FEATURE:
<223> OTHER INFORMATION: Synthetic Primer - STOP mut reverse

<400> SEQUENCE: 14
gttcctggca ccgtttaccc aaagcttgcg c                             31

<210> SEQ ID NO 15
<211> LENGTH: 48
<212> TYPE: DNA
<213> ORGANISM: Artificial Sequence
<220> FEATURE:
<223> OTHER INFORMATION: Synthetic Primer - NdeI mut forward

<400> SEQUENCE: 15
ggcgcaagct ttgggtcaac gcatatggga acgggtatcg gagccacc           48

<210> SEQ ID NO 16
<211> LENGTH: 48
<212> TYPE: DNA
<213> ORGANISM: Artificial Sequence
<220> FEATURE:
<223> OTHER INFORMATION: Synthetic Primer - NdeI mut reverse

<400> SEQUENCE: 16
ggtggctccg atacccgttc ccatatgcgt tgacccaaag cttgcgcc           48
```

```
<210> SEQ ID NO 17
<211> LENGTH: 34
<212> TYPE: DNA
<213> ORGANISM: Artificial Sequence
<220> FEATURE:
<223> OTHER INFORMATION: Synthetic Primer - STOP mut forward

<400> SEQUENCE: 17
tcatggaaca ctcctggtta gatcaaggac gcat                              34

<210> SEQ ID NO 18
<211> LENGTH: 34
<212> TYPE: DNA
<213> ORGANISM: Artificial Sequence
<220> FEATURE:
<223> OTHER INFORMATION: Synthetic Primer - STOP mut reverse

<400> SEQUENCE: 18
atgcgtcctt gatctaacca ggagtgttcc atga                              34
```

PEPTIDES AND USES THEREOF

FIELD OF INVENTION

The present invention relates to the field of carbohydrate-binding peptides, particularly monovalent carbohydrate-binding peptides. More specifically the invention relates to monovalent fucose-binding peptides. The peptides may be recombinantly produced or chemically synthesized. Preferably the peptides are derived from a lectin, in particular *Aleuria aurantia* lectin. Furthermore the invention relates to methods for producing the peptides, assays using the peptides for diagnosis of disorders, as well as methods using the peptides for separation and detection of fucose-containing compounds.

BACKGROUND OF THE INVENTION

Lectins are a class of proteins of non-immune origin that binds carbohydrates without modifying them. They are involved in many recognition events at molecular and cellular levels. Since lectins differ in the types of carbohydrate structures they can recognize they are used to detect and separate cells, bacteria, and viruses with different carbohydrate content. Lectins are also useful tools for investigating the structure, distribution and function of different carbohydrate chains on glycoproteins and glycolipids [Liljeblad et al., 2002; Rudiger et al., 2001; Yamashita et al., 1985].

The *Aleuria aurantia* lectin (AAL) from the fruit bodies of *Aleuria aurantia* mushroom has been extensively used in structural studies of oligosaccharides. AAL is specific for L-fucose and differs from other fucose-binding lectins by having a broad specificity towards fucosylated oligosaccharides [Debray et al., 1989; Fukumori et al., 1989; Kochibe et al., 1980; Nagata et al., 1991]. AAL can bind to oligosaccharides with fucose in $\alpha$1-2, $\alpha$1-3, $\alpha$1-4 and $\alpha$1-6 linkages, with the strongest affinity towards fucose in $\alpha$1-6 linkage, but is relatively insensitive to structural differences in the oligosaccharide backbone [Debray et al., 1989; Wimmerova et al., 2003]. Since AAL is one of the few fucose-binding lectins with a preferential binding to $\alpha$1-6 linked fucose it has been widely used in fractionation of glycoproteins with core-fucosylated complex-type N-glycans. Since changes in fucosylation is often associated with inflammatory conditions and oncogenic transformation AAL has also been used for fractionation and analysis of disease-associated glycosylation [Rydén et al., 1999; Rydén et al., 2002; Rydén et al., 2002]. Native AAL has been shown to agglutinate human erythrocytes of both A, B and 0 subtypes [Fukumori et al., 1989]

Recombinant AAL has been produced by expression in both *E. coli* and *Pichia Pastoris*, and subsequent purification. The recombinant forms of AAL have been shown to retain their agglutinating properties [Amano et al., 2003;].

AAL is a non-glycosylated protein that has a molecular weight of 72 kDa and is composed of two identical 312 amino acid subunits [Kochibe et al., 1980]. The lectin was recently crystallized and each monomer was shown to have a six fold $\beta$-propeller structure with five binding sites for L-fucose [Fujihashi et al., 2003; Wimmerova et al., 2003]. The slight structural differences at the five binding sites as well as the results from site specific mutagenesis studies indicated that the five possible binding sites for fucose differ in affinities towards fucose [Amano et al., 2003; Fujihashi et al., 2003; Wimmerova et al., 2003]. Site 2 and 4 seems to have the highest affinity towards fucose, site 1 to have medium affinity whereas site 3 and 5 seems to bind fucose with the weakest affinity [Fujihashi et al., 2003; Wimmerova et al., 2003].

Lectin-oligosaccharide interactions are generally characterized by a weak affinity (millimolar range) for monovalent binding. This low affinity is usually compensated by the fact that most lectins are multivalent. In contrast, several bacterial and fungal lectins have been shown to display unusually high affinity towards carbohydrate ligands compared to plant or animal lectins, with $K_d$-values in the micromolar range [Imberty et al., 2005; Kostlanova et al., 2005; Tateno et al., 2004]. A further understanding of the binding properties of these lectins will be important for designing high-affinity carbohydrate-binding proteins.

The multivalent nature of plant lectins is important for creating high avidity binding in nature. But the fact that most lectins show variation in binding affinity and binding specificity between different binding sites in the molecule presents problems, especially when plant lectins are used for diagnostic and preparative purposes.

Several diagnostic assays have been developed which measure pathological changes in carbohydrate composition using plant lectins as reagents [Hashimoto et al., 2004; Rydén et al., 1999; Rydén et al., 2002; Rydén et al., 2002]. However, since most target glycoproteins express multimers of the carbohydrate ligand and the lectins employed are multimeric in nature, linear relationships between expressed antigen and amount of bound lectin is seldom obtained. Thus these assays are usually only diagnostically relevant in a limited part of a concentration range.

There have been few previous attempts to produce monovalent carbohydrate-binding lectins. Procedures for preparing reduced valency Concanavalin A (a mannose and glucose-binding lectin) includes chemical modification such as succinylation and/or photoaffinity labelling (Fraser et al, 1976, Beppu et al 1976, Beppu et al 1975, Tanaka et al 1981, Gunther et al 1973,). Monovalent forms of Concanavalin A have also been prepared by proteolytic digestion (Wands et al 1976,). These methods were referred to in a previous patent application (WO9855869A1). Monovalent forms of the sialic acid-binding lectins *Sambucus sieboldiana* and *Maackia amurensis* as well as the galactose-binding lectin *Anthocidaris crassispina* and the Gal-NAc-binding lectin Wistaria floribunda have been prepared by disulfide-bridge reduction and subsequent protection with iodoacetamide (Kaku and Shibuya 1992, Kaku et al 1993, Ozeki 1991, Kurokawa 1976). These methods are not generally applicable to other lectins, and would not work to produce monovalent binding peptides from fucose-binding lectins such as *Aleuria aurantia*. No prior art of producing recombinant monovalent fucose-binding lectin peptides has been found. In a study of peptides containing GlcNAc-binding hevein domains Espinosa and co-workers [Espinosa et al, 2000] used a monovalent form of wheat-germ agglutinin—the isolated B-domain (WGA-B). They found that WGA-B retained its binding capacity towards chitotriose but that the binding affinity was too low to be considered useful for practical purposes (millimolar range).

Carbohydrate-binding peptides in prior art struggle with at least three problems arising from the multivalent nature of these peptides. Firstly, the problem of agglutination when carbohydrate-binding peptides bind more than one carbohydrate-expressing entity. This is a major drawback in cell surface e analysis of carbohydrates by flow cytometry, where concentrations of lectin have to be kept below agglutinating concentration, thereby significantly hampering sensitivity of the assay. Secondly, the problem of not achieving a linear relationship between carbohydrate expression and lectin-binding in more than just a limited part of a concentration range in an assay. Thirdly, the individual binding sites in multimeric lectins such as *Aleuria aurantia* differ in binding affinity and specificity towards carbohydrate ligands, which makes them unreliable for diagnostic purposes.

SUMMARY OF THE INVENTION

The present invention meets at least partly needs of prior art by providing isolated monovalent fucose-binding peptides, methods for productions thereof, assays using the peptides for diagnosis of disorders, as well as methods using the peptides for separation and detection of fucose-containing compounds. The peptides of the invention prevent agglutination and simultanously show reasonable binding affinities (micromolar range). Furthermore the peptides enable linear relationships between carbohydrate expression and lectin binding, thus enhancing the diagnostic range of an assay and the further applicability in biotechnological fields. Furthermore the peptides show a narrower specificity range than the native lecin.

In a first aspect the present invention relates to isolated monovalent fucose-binding peptides. In preferred embodiments the peptides are derived from lectin or show at least 80% homology to a lectin.

In one embodiment the peptides are derived from *Aleuria aurantia* lectin. In another embodiment the peptides comprise amino acid sequences showing at least 80% homology to the *Aleuria aurantia* lectin domains Mono-F1 (SEQ ID NO: 2), Mono-F2 (SEQ ID NO: 4), Mono-F3 (SEQ ID NO: 6), Mono-F4 (SEQ ID NO: 8) and Mono-F5 (SEQ ID NO: 10), respectively, particularly the Mono-F2 (SEQ ID NO: 4) domain.

The invention further provides nucleic acid molecules coding for peptides of the invention, vectors comprising the nucleic acid molecules and host cells comprising the vectors. The nucleic acid sequences encoding Mono-F1, Mono-F2, Mono-F3, Mono-F4 and Mono-F5 are given as SEQ ID NOs: 1, 3, 5, 7 and 9, respectively, in the appended sequence listing.

In another aspect the invention relates to methods for producing peptides according to the invention, in which abovementioned host cells are cultivated and peptides isolated.

Furthermore the invention relates to assays for the diagnosis of disorders as well as to methods for separation and detection of fucose-containing compounds.

Definitions

With "AAL" is meant *Aleuria aurantia* lectin, i.e. lectin derived from the *Aleuria aurantia* mushroom.

With "fucose-containing compounds" is meant fucose or any free oligosaccharide or oligosaccharide conjugated or bound to an aglycon such as polypeptide, lipid, biomolecule or mechanical support, containing one or more fucose residues.

With "ability to bind fucose and/or fucose containing compounds" is meant an ability to bind with a binding affinity with $K_d$ of less than 100 µM, if not otherwise specified.

By "peptides having X % identity to a sequence" is meant peptides, in which one or more amino acid residues have been added, deleted, replaced, or chemically modified, but where at least X % of the amino acids are the same as in the specified amino acid sequence. Algorithms for computing such percentages of identity are known in the art, e.g. CLUSTAL W.

The term "comprising" shall be construed as open, i.e. an entity comprising a certain matter may also contain further matter.

The term "consisting" shall be construed as closed, i.e. an entity consisting of certain matter does not include any further matter.

For the purposes of this disclosure, the definition of an entity as comprising certain subject matter shall be construed as including the specific case of the same entity consisting of said subject matter.

BRIEF DESCRIPTION OF THE DRAWINGS AND TABLES

FIG. 1 - Amino acid sequence of Mono-F2 (SEQ ID NO: 4). Amino acids 1-16 (italic) correspond to his-tag and thrombin recognition site. Amino acids 17-127 (bold) correspond to AAL sequence (aa 51-161).

Arrow indicate thrombin cleavage site. The calculated molecular weight of Mono-F2 (SEQ ID NO: 4) is 14037 Da. The calculated molecular weight of Mono-F2 (SEQ ID NO: 4) without the His-tag is 12141 Da.

FIG. 2 - Nucleotide sequence of Mono-F2 (SEQ ID NO: 4). Sequence in italic corresponds to start codon (ATG) and sequence coding for his-tag and thrombin recognition site. Bold sequence corresponds to sequence encoding Ser51 to Gly161 in native AAL.

FIG. 3 - SDS-PAGE analysis of purified Mono-F2 (SEQ ID NO: 4)
1. Purified his-tagged Mono Mono-F2 (SEQ ID NO: 4)-approximately 17 kDa
2. Blank
3. Cell culture supernatant
4. Native AAL FIG. 4 - Oligosaccharide affinity analysis of Mono-F2 (SEQ ID NO: 4) using surface plasmon resonance analysis (BIACORE). Figure A shows sensorgrams for binding of a glycopeptide carrying one B-tri epitope (B-tri-KE2) to immobilized Mono-F2 (SEQ ID NO: 4). The sensorgrams were obtained by injection of B-tri KE2 in concentrations of (from bottom to top curve) 0.05, 0.1, 1, 2, 5, 10, 25, 50, 75, and 100 µM. Figure B shows the steady state analysis of the interaction of B-tri KE2 with sensor-bound Mono-F2. ΔRU values determined from the steady state plateau region were plotted as a function of analyte concentration, and the data was fitted by nonlinear regression according to a single site Langmuir binding model. The obtained Kd-value for the interaction was 31 µM.

Figure 5:
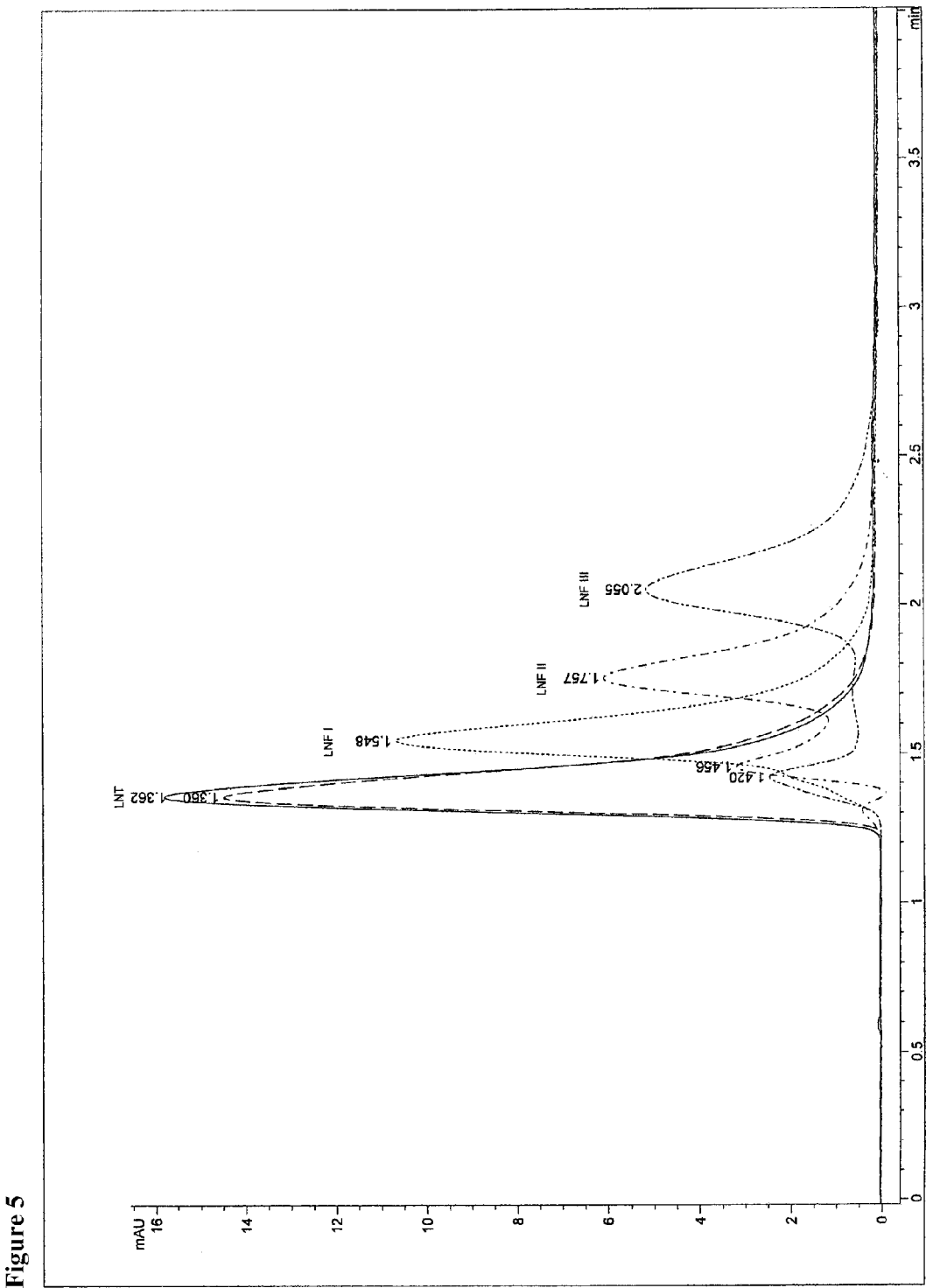

FIG. 5 - chromatograms of some fucosylated human milk oligosaccharides (LNnF I, LNF II and LNF III) and a non-fucosylated control (LNT) on a silica column with immobilized Mono-F2 (SEQ ID NO: 4).

FIG. 6 - Table showing oligosaccharide structures.

Figure 7:
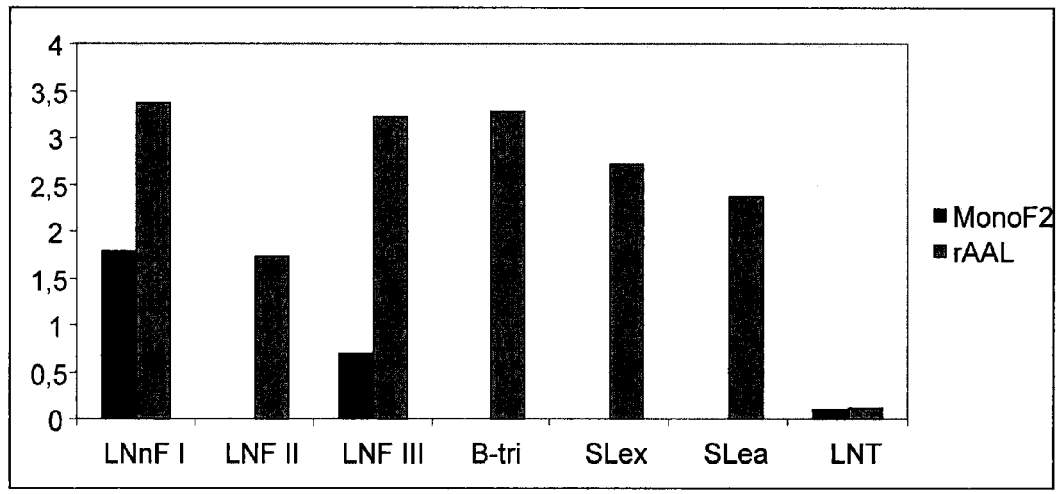

FIG. 7 - Differences in specificity of binding between Mono-F2 (SEQ ID NO: 4) and recombinant full length AAL.

ELISA showing binding of Mono-F2 (SEQ ID NO: 4) and recombinant AAL (rAAL) to oligosaccharide glycoconjugates.

Figure 8:
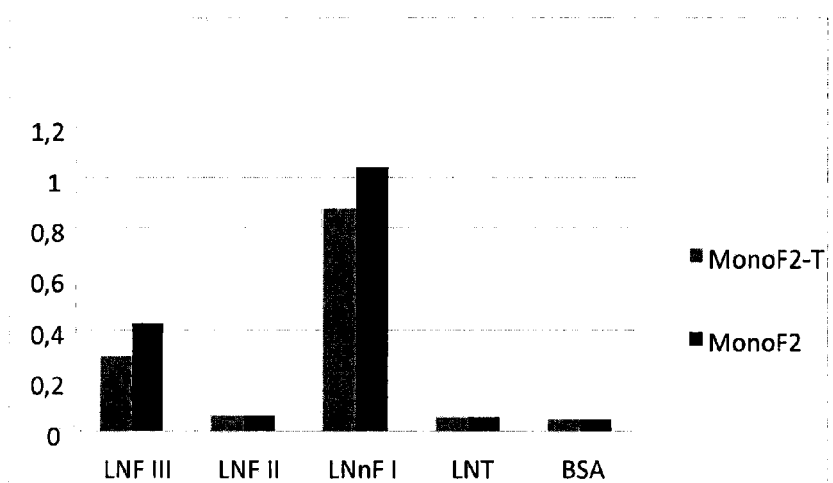

FIG. 8 - Similar binding of Mono-F2 (SEQ ID NO: 4) with and without His-tag in binding to fucosylated oligosaccharides.

ELISA showing binding of Mono-F2 (SEQ ID NO: 4) with (Mono F2) or without (MonoF2-T) His-tag to oligosaccharide glycoconjugates.

DETAILED DESCRIPTION OF THE INVENTION

Using a small monovalent carbohydrate-binding peptide would set aside the agglutination tendency and enable linear relationships between carbohydrate expression and lectin binding, thus enhancing the diagnostic range of an assay. Monovalent carbohydrate-binding peptides with reasonable binding affinities (less than 100 µM) would consequently provide important reagents that could be valuable for diagnostic and therapeutic purposes as well as in biotechnological applications. However, previous attempts to use monovalent carbohydrate-binding peptides have failed due to low binding affinities of these peptides.

Thus, in a first aspect the present invention provides isolated monovalent fucose-binding peptides. In one embodiment the peptides are derived from lectins.

Crystallization analysis has shown that AAL forms dimers of two structurally identical subunits. The three-dimensional structure of each subunit is arranged as six "blades" of four-stranded anti-parallel β-sheet structural elements in a cylindrical arrangement. A so called "six-bladed β-propeller fold". The fucose binding sites are located between two consecutive blades as pockets at the external face of the cylinder. Since the overall three-dimensional structure of the five fucose binding sites are similar, it should be possible to construct monovalent fucose-binding peptides corresponding to all five individual binding sites in AAL.

Since it is likely that the different binding sites differ in terms of binding specificity and affinity, the use of monovalent fucose-binding peptides will provide more specific reagents for diagnostic and separation purposes.

In another embodiment the invention relates to isolated monovalent fucose-binding peptides derived from *Aleuria aurantia* lectin (AAL), in particular peptides comprising an amino acid sequence of any of the AAL fucose-binding sites Mono-F1 (SEQ ID NO: 2), Mono-F2 (SEQ ID NO: 4), Mono-F3 (SEQ ID NO: 6), Mono-F4 (SEQ ID NO: 8) and Mono-F5 (SEQ ID NO: 10), respectively.

In still another embodiment the invention relates to a peptide comprising the site 2 of AAL (Mono-F2, SEQ ID NO: 4) or a peptide showing at least 80% homology thereto. It was found that this monovalent peptide retains the ability to bind fucosylated oligosaccharides with micromolar affinities. Furthermore the Mono-F2 (SEQ ID NO: 4) site preferentially binds fucose linked α1-2 as opposed to the native AAL molecule that preferentially bind fucose linked α1-6.

It is envisioned that the peptides derived from naturally occurring lectins, such as AAL, may retain some or all of their fucose-binding ability also if some amino acid residues in the peptides are deleted or changed, or if further amino acid residues are inserted or added. The invention includes all such variants, and especially such variants the amino acid sequence of which retain a certain percentage of identity to the amino acid sequence of the naturally occurring lectin sequence, such as 80%, 85%, 90%, 95% or 98%.

Furthermore the peptide of the invention has a binding affinity for fucose with a Kd value of less than 100 μM, more preferably less than 50 μM and most preferred less than 10 μM.

In still another embodiment the invention is related to monovalent fucose-binding peptides for purification, separation and detection, wherein the peptides are conjugated or fused with tags. Tags may be conjugated or fused with peptides of the invention by way of recombinant or chemical procedures, as is known to the skilled person in the art. By tags meaning a peptide such as poly-histidine, FLAG or Myc or a biomolecule such as biotin, with high affinity ($K_d$ less than $10^{-7}$ M) to its ligand. The tag is used in purification of lectin from cell culture using affinity chromatography where the affinity support is conjugated with the tag ligand. This purification procedure renders possible purification of lectin without addition of free fucose to the elution buffers, which may otherways affect lectin properties.

In still another aspect the invention provides nucleic acid sequences coding for the peptides of the invention.

In another aspect the invention relates to recombinant expression vectors comprising the above nucleic acid sequences. Such recombinant vectors may be one capable of being expressed in eukaryotic and prokaryotic hosts. The vector containing, in addition to the above nucleic acid sequences, other sequences such as sequences that are known for expression of the desired sequence and the maintenance and propagation of the vector in the host cell. Constructions of such vectors are known to the skilled person in the art.

In yet another aspect the invention provides host cells comprising the above vectors, the host cells being a mammalian cell, a bacterium, a fungal cell, a yeast cell or an insect cell.

In a further aspect the invention relates to methods for producing the peptides of the invention, comprising the steps of:
  cultivating the above-mentioned host cells, and
  isolating the peptides.

In particular, the invention relates to methods for recombinant production of peptides homologous to the AAL sequence that comprises two consecutive blades with one fucose-binding site in-between, preferably Mono-F2 (SEQ ID NO: 4) site.

A person skilled in the art is familiar with the appropriate conditions for culturing the host cells and isolating the peptides. The peptide can be collected from the host cell medium. On the other hand the peptide can also remain in the host cell and can be isolated from there. When *E.coli* are transformed with a vector encoding Mono-F2 (SEQ ID NO: 4), the resulting Mono-F2 (SEQ ID NO: 4) peptide is present both in soluble form and as insoluble protein aggregates (inclusion bodies). Thus, there are two methods for isolating peptides of the invention from transformed *E. coli*. Soluble peptides of the invention are obtained after sonication of transformed *E. coli*. After centrifugation the supernatant is applied to an affinity column preferentially consisting of a matrix with immobilized ligands towards fused tags on the peptide of the invention. In order to isolate peptides from inclusion bodies the sediment of *E.coli* sonicate is dissolved under reducing and denaturing conditions after removal of soluble proteins. The denatured protein solution is applied to an affinity column. Renaturation is carried out by dilution of the denaturing buffer. Active carbohydrate binding peptide is obtained after elution from the affinity column.

The invention also relates to methods for separation and detection of fucose-containing compounds for diagnostic procedures using a peptide of the invention and/or a chimeric molecule or complex comprising said peptide, as a reagent in diagnostic assays for analysis of disease-associated changes in fucosylation of oligosaccharides on glycosylated proteins in humans or animals.

In one aspect the invention relates to methods for detecting a fucose-containing compound in a sample, comprising the steps of:
i) bringing a peptide of the invention into contact with said sample; and
ii) detecting fucose-containing compound bound to the peptide.

Oligosaccharides are detected by its content of fucose. Altered fucose levels may be seen—as a marker for disease—in a number of pathological processes such as inflammation, infectious disease recognition and neoplastic progression (Listinsky et al 1998)

We have previously shown that fucosylation of the acute phase protein a1-acid glycoprotein is elevated as a consequence of pathological conditions such as chronic inflammatory disease and liver disease. We developed a lectin-based immunoassay for specific measurement of AGP fucosylation. The assay was based on quantization of the number of fucose residues on AGP isolated from patient serum using AAL. Using this assay we could show that elevated AGP fucosylation was a marker for inflammation status in rheumatic patients and furthermore useful for diagnosis of liver fibrosis and cirrhosis. The peptides of the invention would have the potential to further increase specificity and diagnostic detection range of these types of glycodiagnostic assays.

Thus, in one aspect the invention provides an assay for the diagnosis of disorders, such as liver fibrosis, cirrhosis, inflammatory diseases and cancer, comprising the steps of
i) bringing a peptide of the invention into contact with a sample from a patient; and
ii) detecting marker bound to the peptide.

In one application of the invention antibodies directed against AGP are coated in wells of a polystyrene microtiter plate. Diluted serum or plasma are added to the wells and AGP is captured on the antibodies in the wells. After washing, the peptide of the invention covalently conjugated with a tag for detection such as biotin is added to the wells. After additional washing horse-radish peroxidase (HRP) labeled streptavidin are added. HRP will catalyze the conversion of a substrate to a colored substance and the amount of color in the wells is proportional to the fucose level on AGP (Rydén et al 1999).

The invention also relates to the use of the peptides of the invention for separation and detection of fucose-containing compounds in laboratory or industrial use. The separation and detection procedures may be used for purification of fucose-containing compounds.

In another aspect the invention provides a method for separation of fucose-containing compounds from other compounds comprising the steps of
i) bringing a peptide of the invention, bound to a solid phase, into contact with a fucose-containing compound;
ii) allowing the fucose-containing compound to bind to the solid phase by for example applying a sample containing a mixture of fucosylated oligosaccharides to a column packed with the solid support.
iii) washing the column with buffer. Separation based on weak affinity interaction can be obtained with isocratic elution using the same buffer as the samples was dissolved in.
iv) dissociating of high affinity interactions is obtained by elution with increasing concentrations of free monosaccharide (fucose) or other dissociating agents.

EXAMPLES

The invention will now be described by way of the following non-limiting examples and accompanying drawings.

Example 1

Construction of Plasmid, Expression and Purification of a His-tagged form of a monovalent fucose-binding AAL fragment (Mono-F2, SEQ ID NO: 4).

A pET-28b-plasmid containing cDNA encoding full length His-tagged AAL was obtained as described (Olausson et al. 2008). A pET-28b-plasmid containing cDNA encoding Mono-F2 (SEQ ID NO: 4) was obtained by:
1. Insertion of a NdeI restriction enzyme cleavage site at nucleotide position 150 in the AAL coding sequence.
2. Insertion of a stop codon site at nucleotide position 480 in the AAL coding sequence to remove the 3' segment of AAL corresponding to nucleotides 481-939.
3. Restriction enzyme cleavage of the plasmid with NdeI to remove the 5' segment of AAL corresponding to nucleotides 1-150.
4. Ligation of the plasmid using T4 ligase.

The amino acid sequence of the His-tagged form of Mono-F2 (SEQ ID NO: 4) and its corresponding cDNA sequence are shown in FIG. 1 and FIG. 2. The cDNA sequence was confirmed by Sanger dideoxy sequencing.

Site specific mutagenesis was performed using Quick-Change Multi Site-Directed Mutagenesis kit from Stratagene (La Jolla, Calif.). The primers used are shown below.

| Primer | Nucleotide sequence |
|---|---|
| NdeI mut forward | 5' GGAGACAATCCATGGACCGGCCATATGAGC CAGAATGTAATCGGCG 3' (SEQ ID NO: 11) |
| NdeI mut reverse | 5' CGCCGATTACATTCTGGCTCATATGGCCG GTCCATGGATTGTCTC 3' (SEQ ID NO: 12) |
| STOP mut forward | 5' GCGCAAGCTTTGGGTAAACGGTGCCAGGAAC 3' (SEQ ID NO: 13) |
| STOP mut reverse | 5' GTTCCTGGCACCGTTTACCCAAAGCTTGCGC 3' (SEQ ID NO: 14) |

The resulting plasmid was transformed into the *E. coli* strain BL21/DE3 (Invitrogen). BL21/DE3 harbouring the recombinant pET-28b-Mono-F2 plasmid was added to 500 mL of LB-medium containing 30 μg/mL kanamycin and incubated at 37° C. with shaking until $OD_{600}$ was between 0.6-0.9. To induce the synthesis of Mono-F2 (SEQ ID NO: 4), isopropyl-beta-D-thiogalactopyranoside (IPGT) was added to a final concentration of 0.5 mM and the cells were incubated at room temperature over night with shaking. Cells were collected by centrifugation and sonicated for 4×30 seconds in 10 mM phosphate buffer saline, pH 7.2 (PBS). The sonicate was centrifuged first at 3200 g for 20 minutes then at 19000 g for 15 minutes both at 4° C. to remove debris. The supernatant containing Mono-F2 (SEQ ID NO: 4) was purified by affinity chromatography using a 1 mL Ni-column (HiTrapTM Chelating HP column, Amersham Biosciences, Uppsala, Sweden) at a flow rate of 1 mL/min.

Purified Mono-F2 was analyzed by SDS-PAGE and migrated as a single band with a molecular weight of approximately 14 kDa. The result is shown in FIG. 3.

Example 2

In Contrast to Full Length raal Mono-F2 (SEQ ID NO: 4) does not Agglutinate Red Blood Cells Confirming its Monovalent Nature The hemagglutination activity of full length rAAL and Mono-F2 (SEQ ID NO: 4) was determined by serial dilutions of the lectins in PBS and mixing with an equal volume (50μL) of 2% human type 0erythrocytes suspended in PBS. After incubation at room temperature for 1h the minimum lectin concentration that gave a positive reaction was determined. The minimal concentration of rAAL to produce hemagglutination was 2.5μg/ml (~71 nM) whereas Mono-F2 (SEQ ID NO: 4) did not give hemagglutination even in concentrations up to 200 μg/ml (~14000 nM).

Example 3

Affinity Chromatography Shows High Affinity Binding of Mono-F2 (SEQ ID NO: 4) to Immobilized Fucose Purified Mono-F2 (SEQ ID NO: 4) was analyzed on a 1 mL fucose-agarose column (Sigma-Aldrich, Stockholm, Sweden). The column was equilibrated with 20mL PBS. Mono-F2 (SEQ ID NO: 4) was added and the column was incubated for 20 minutes at 4° C. with gentle rocking. After incubation the column was washed with PBS until the absorbance at 280 nm had reached zero. Elution was performed with 4 mL of 0.15 M L-fucose in PBS, 4 mL of 1 M L-fucose in PBS, and lastly with glycine buffer pH 2.5. Fractions (1 mL) were collected with monitoring of absorbance at 280 nm. The fractions were further analysed by SDS-PAGE. The analysis showed that Mono-F2 could not be eluted with 0.15 M fucose. Very little was eluted with 1 M fucose. A low-pH buffer had to be used to get full elution of Mono-F2 (SEQ ID NO: 4) from the fucose-agarose column indicating high affinity binding to fucose.

Example 4

Biacore Analysis Shows Binding of Fucosylated Oligosaccharides to Immobilized Mono-F2 (SEQ ID NO: 4) in the μM range.

Surface Plasmon resonance (SPR) measurements were performed using a Biacore 2000 (BiacoreAB, Uppsala, Sweden) at 25° C. with PBS as running buffer and a flow rate of 5 μL/min. Channel two contained Mono-F2 (SEQ ID NO: 4) (6748 RU) whereas channel one was used as the control flow cell. A research grade CM5 sensor chip was activated with a 1-ethyl-3-(3-(dimethylamino)propyl)carbodiimide/Nhydroxysuccinimide solution for 7 min. Then 10 μL of 1.1 μM Mono-F2 (SEQ ID NO: 4) in acetate buffer (pH 5.0) was injected into flow cell two. The unreacted species on the sensor surface were blocked by a 35 μL injection of 1 M ethanolamine. The blank channel was treated identically except for the lectin injection. Then 30 μL of carbohydrate or glycopeptide solutions (concentrations between 0.001 and 150 μM) in running buffer were injected into the flow cells using the kinject mode. The equilibrium response (after subtraction from the response of the reference surface) of each experiment was used to create curves of analyte binding, which were fitted to a 1:1 steady-state affinity model using Scrubber version 2.0 software (Biologic Software Pty Ltd, Campbell, Australia). When using a synthesized glycopeptide glycosylated in a single site with the B-tri oligosaccharide (Fucα1-2[Galα1-3]Galβ1-) the sensorgrams obtained revealed an affinity ($K_d$) of Mono-F2 (SEQ ID NO: 4) towards the fucosylated oligosaccharide of 16 μM. The results are shown in FIG. 4.

Example 5

Oligosaccharide Affinity Chromatography Shows that Mono-F2 (SEQ ID NO: 4) could be Immobilized to Solid Support and Function as Separation Matrix for Fucosylated Oligosaccharides Mono-F2 (SEQ ID NO: 4) was immobilized on silica particles (5μM, 300 Å) and packed in an affinity column (50× 0.32 mm) and chromatography of a number of oligosaccharides were examined. LNF I, LNF II and LNF III was retarded on the column with increasing retention times whereas LNT (non fucosylated) was not bound to the column. The results are shown in FIG. 5. Elutions of oligosaccharides were detected by UV absorbance at 210 nm.

Example 6

Mono-F2 (SEQ ID NO: 4) Shows a More Restricted Oligosaccharide Binding Profile Compared to rAAL.

Purified Mono-F2 (SEQ ID NO: 4) and full length rAAL were biotinylated using IMMUNOPROBE™ Biotinylation Kit (Sigma-Aldrich, Stockholm, Sweden) according to the manufacturer's instruction. The biotin/protein ratio was determined to 1.1 biotin moieties per protein molecule for both Mono-F2 (SEQ ID NO: 4) and rAAL. Microtiter plates (Nunc MaxiSorp™ eBioscience, San Diego, CA) were coated with 0.2 μg of LNnF I-BSA, LNF II-BSA, LNF III-HSA, LNT-BSA; 0.1 μg of B-tri-HSA, SLex-HSA and SLea-HSA in 100 μL coating buffer (15 mM $Na_2CO_3$, 35 mM $NaHCO_3$, 0.02% $NaN_3$, pH 9.6). Then 100 μL of biotinylated Mono-F2 (SEQ ID NO: 4) or full length rAAL was added to the wells. After addition of ExtrAvidin (E-2632 Sigma-Aldrich, Stockholm, Sweden) and phosphatase substrate (Sigma 104®, Sigma-Aldrich, Stockholm, Sweden) the amount of Mono-F2 (SEQ ID NO: 4) or full length AAL binding to each well were measured at 405 nm using a $VERSA_{max}$ microplate reader (Molecular Devices Corporation, Sunnyvale, CA).

Structures of the analyzed oligosaccharides are depicted in FIG. 6.

Both rAAL and Mono-F2 (SEQ ID NO: 4) showed only low background binding to the non-fucosylated oligosaccharide LNT. rAAL bound to all fucosylated oligosaccharides in the ELISA assay, whereas Mono-F2 (SEQ ID NO: 4) showed a much more restricted binding specificity binding only non-sialylated oligosaccharide structures with α1-2 or α1-4 linked fucose (FIG. 7). This may make it suitable for detecting disease-related changes such as hyper-fucosylation of glycoproteins in liver disease, and cancer.

Example 7

Removal of His-tag from Mono-F2 (SEQ ID NO: 4) does not Affect its Binding Activity To analyze whether the His-tag on Mono-F2 (SEQ ID NO: 4) affected the fucose binding the ELISA analysis was also performed using Mono-F2 (SEQ ID NO: 4) pre-treated with thrombin protease to remove the His-tag. Biotin labelled Mono-F2 (SEQ ID NO: 4) (50μg) in PBS was incubated with 2 units of thrombin protease (Amersham Biosciences, Uppsala, Sweden) for 2 hours at room temperature. SDS-PAGE analysis of Mono-F2 (SEQ ID NO: 4) after thrombin treatment showed a single band with a molecular weight about 2000 Da lower than for non treated rAAL confirming complete cleavage of the His-tag. ELISA analysis using the thrombin treated Mono-F2 (SEQ ID NO: 4) (Mono-F2-T) showed identical binding as non-treated Mono-F2 (SEQ ID NO: 4) to LNnF I-, LNF II- and LNF III-BSA conjugates indicating that the His-tag does not contribute to the binding of fucosylated oligosaccharides (FIG. 8).

Example 8

Construction and Expression of a Plasmid Coding for a His-Tagged Form of a Second AAL Fragment (Mono-F4, SEQ ID NO: 8).

A pET-28b-plasmid containing cDNA encoding Mono-F4 (SEQ ID NO: 8) was obtained exactly as for Mono-F2 (SEQ ID NO: 4) (Example 1). Except that the primers used were the following:

| Primer | Nucleotide sequence |
|---|---|
| NdeI mut forward | 5'-GGCGCAAGCTTTGGGTCAACGCATATGGG AACGGGTATCGGAGCCACC-3' (SEQ ID NO: 15) |
| NdeI mut reverse | 5'-GGTGGCTCCGATACCCGTTCCCATATGCG TTGACCCAAAGCTTGCGCC-3' (SEQ ID NO: 16) |
| STOP mut forward | 5'-TCATGGAACACTCCTGGTTAGATCAAGGA CGCAT-3' (SEQ ID NO: 17) |
| STOP mut reverse | 5'-ATGCGTCCTTGATCTAACCAGGAGTGTTC CATGA-3' (SEQ ID NO: 18) |

References

Amano K, Takase M, Ando A, Nagata Y. 2003. Production of functional lectin in *pichia pastoris* directed by cloned cDNA from *Aleuria aurantia*. *Biosci Biotechnol Biochem.* 67: 2277-2279.

Beppu M, Terao T, Osawa T. 1976 Preparation of monovalent succinyl-concanavalin A and its mitogenic activity. J. Biochem. 79:1113-7.

Beppu M, Terao T, Osawa T. 1975. Photoaffinity labeling of concanavalin A. Preparation of a Concanavalin a Derivative with Reduced Valence. J. Biochem. 1975 November; 78(5):1013-9.

Debray H, Montreuil J. 1989. *Aleuria aurantia* agglutinin. A new isolation procedure and further study of its specificity towards various glycopeptides and oligosaccharides. *Carbohydr Res.* 185: 15-26.

Espinosa J F, Asensio J L, Garcia J L, Laynez J, Bruix M, Wright C, Siebert H C, Gabius H J, Canada F J, Jimenez-Barbero J. 2000. NMR investigations of protein-carbohydrate interactions binding studies and refined three-dimensional solution structure of the complex between the B domain of wheat germ agglutinin and N,N', N"-triacetyl-chitotriose. *Eur J. Biochem.* 267: 3965-78.

Fraser A R, Hemperly J J, Wang J L, Edelman G M. 1976 Monovalent derivatives of concanavalin A. Proc Natl Acad Sci USA. 73:790-4.

Fujihashi M, Peapus D, Kamiya N, Nagata Y, Miki K. 2003. Crystal structure of fucose-specific *Aleuria aurantia* binding ligands at three of its five recognition sites. *Biochem.* 42: 11093-11099.

Fukumori F, Takeuchi N, Hagiwara T, Ito K, Kochibe N, Kobata A, Nagata Y. 1989. Cloning and expression of a functional fucose-specific lectin from an orange peel mushroom, *Aleuria aurantia*. *FEBS Lett.* 2: 153-156.

Gunther G R, Wang J L, Yahara I, Cunningham B A, Edelman G M. 1973 Concanavalin A derivatives with altered biological activities. Proc Natl Acad Sci USA. 70:1012-6.

Hashimoto, S., Asao, T., Takahashi, J., Yagihashi, Y., Nishimura, T., Saniabadi, A. R., Poland, D. C., van Dijk, W., Kuwano, H., Kochibe, N. and Yazawa, S. (2004) alpha1-acid glycoprotein fucosylation as a marker of carcinoma progression and prognosis. *Cancer.* 101: 2825-2836

Imberty A, Mitchell E, Wimmerova M. 2005. Structural basis of high-affinity glycan recognition by bacterial and fungal lectins. *Curr Opin Struct Biol.* 15: 525-534.

Kaku H, Mori Y, Goldstein I J, Shibuya N. 1993. Monomeric, monovalent derivative of Maackia amurensis leukoagglutinin Preparation and application to the study of cell surface glycoconjugates by flow cytometry. J Biol. Chem. 268: 13237-41.

Kaku H, Shibuya N. 1992. Preparation of a stable subunit of Japanese elderberry (*Sambucus sieboldiana*) bark lectin and its application for the study of cell surface carbohydrates by flow cytometry. FEBS Lett. 306:176-80.

Kochibe N, Furukawa K. 1980. Purification and properties of a novel fucose-specific hemagglutinin of *Aleuria aurantia*. *Biochem.* 19: 2841-2846.

Kostlánová N, Mitchell E, Lortat-Jacob H, Oscarson S, Lahmann M, Gilboa-Garber N, Chambat G, Wimmerová M, Imberty A. 2005. The fucose-binding lectin from *Ralstonia solanacearum*: a new type of β-propeller architecture formed by oligomerisation and interacting with fucoside, fucosyllactose and plant xyloglucan, *J Biol. Chem.* 280: 27839-27849.

Kurokawa T, Tsuda M, Sugino Y. 1976 Purification and characterization of a lectin from *Wistaria floribunda* seeds. *J Biol. Chem.* 251:5686-93.

Liljeblad M, Lundblad A, Påhlsson P. 2002. Analysis of glycoproteins in cell culture supernatants using a lectin immunosensor technique. *Biosens Bioelectron.* 17: 883-891.

Listinsky J J, Siegal G P, Listinsky C M. 1998. -L-Fucose. Am J Clin Pathol 110: 425-40.

Nagata Y, Fukumori F, Sakai H, Hagiwara T, Hiratsuka Y, Kochibe N, Kobata A. 1991. Crystallization and characterization of a lectin obtained from a mushroom, *Aleuria Aurantia*. *Biochim Biophys Acta.* 29: 187-190.

Olausson J, Tibell L, Jonsson B H, Påhlsson P. 2008. Detection of a high affinity binding site in recombinant *Aleuria aurantia* lectin. *Glycoconjugate J.* 25:753-62

Ozeki Y, Yokota Y, Kato K H, Titani K, Matsui T. 1995. Developmental expression of D-galactoside-binding lectin in sea urchin (*Anthocidaris crassispina*) eggs. Exp Cell Res. 216:318-24.

Rudiger H, Gabius H J. 2001. Plant lectins: Occurrence, biochemistry, functions and applications. *Glycoconj J.* 18: 589-613.

Ryden I, Lundblad A, Påhlsson P. 1999. Lectin ELISA for analysis of α1-acid glycoprotein fucosylation in the acute phase response. *Clin Chem.* 45: 2010-2012.

Ryden I, Påhlsson P, Lindgren S. 2002. Diagnostic accuracy of alpha(1)-acid glycoprotein fucosylation for liver cirrhosis in patients undergoing hepatic biopsy. *Clin Chem.* 48: 2195-2201.

Ryden I, Påhlsson P, Lundblad A, Skogh T. 2002. Fucosylation of a 1-acid glycoprotein (orosomucoid) compared with traditional biochemical markers of inflammation in recent onset rheumatoid arthritis. *Clin Chem. Acta.* 317: 221-229.

Tateno H, Winter H, Goldstein I. 2004. Cloning, expression in *Escherichia coli* and characterization of the recombinant Neu5Acα2,6Galβ1, 4GlcNAc-specific high-affinity lectin and its mutants from the mushroom *Polyporus squamosus*. *Biochem J.* 382: 667-675.

Wands J R, Podolsky D K, Isselbacher K J. 1976. Mechanism of human lymphocyte stimulation by concanavalin A: role of valence and surface binding sites. Proc Natl Acad Sci USA. 1976 June; 73(6):2118-22.

Wimmerova M, Mitchell E, Sanchez J, Gautier C, Imberty A. 2003. Crystal structure of fungal lectin. *J Biol. Chem.* 278: 27059-27067.

Yamashita K, Kochibe N, Ohkura T, Ueda I, Kobata A. 1985. Fractionation of L-fucose-containing oligosaccharides on immobilized *Aleuria aurantia* lectin. *J. Biol. Chem.* 8: 4688-4693.

The inventions claimed is:

1. An isolated monovalent fucose-binding peptide, comprising a monovalent fucose-binding site of *Aleuria aurantia* lectin, and an amino acid sequence having at least 80% identity to a sequence selected from the group consisting of: SEQ ID NO: 2, SEQ ID NO: 4, SEQ ID NO: 6, SEQ ID NO: 8, and SEQ ID NO: 10.

2. The peptide according to claim 1, wherein the sequence is SEQ ID NO: 4.

3. The peptide according to claim 1 having a binding affinity for fucose with a Kd value of less than 100 μM.

4. The peptide according to claim 1, having a binding affinity for fucose with a Kd value of less than 50 μM.

5. The peptide according to claim 1, having a binding affinity for fucose with a Kd value of less than 10 μM.

6. The peptide according to claim 1, further comprising a tag for separation and/or detection.

7. The peptide according to claim 1, wherein said binding site comprises an amino acid sequence having at least 90% identity to a sequence selected from the group consisting of: SEQ ID NO: 2, SEQ ID NO: 4, SEQ ID NO: 6, SEQ ID NO: 8, and SEQ ID NO: 10.

8. The peptide according to claim 1, wherein said binding site comprises an amino acid sequence having at least 95% identity to a sequence selected from the group consisting of: SEQ ID NO: 2, SEQ ID NO: 4, SEQ ID NO: 6, SEQ ID NO: 8, and SEQ ID NO: 10.

9. The peptide according to claim 1 produced as a fusion protein.

10. A isolated nucleic acid molecule coding for the peptide according to claim 1.

11. A vector comprising the nucleic acid molecule according to claim 10.

12. A host cell comprising the vector according to claim 11.

13. A method for producing an isolated monovalent fucose-binding peptide comprising the steps of:
   cultivating the host cell according to claim 12 under conditions suitable for expression of said peptide; and
   isolating said peptide.

14. A method for detecting a fucose-containing compound in a sample, comprising the steps:
   i) bringing a peptide according to claim 1 into contact with said sample; and
   ii) detecting said fucose-containing compound bound to said peptide.

15. The method according to claim 14, wherein the sample is derived from a human or animal patient and the fucose-containing compound is a marker for liver fibrosis or cirrhosis, inflammatory disease or cancer.

16. The method according to claim 15, wherein the marker is α1-acid glycoprotein.

17. A method for separation of fucose-containing compounds from a sample, comprising the steps of:
   i) bringing a peptide according to claim 1 into contact with the fucose-containing compound in the sample;
   ii) allowing the fucose-containing compound to bind to said peptide;
   iii) separating the fucose-containing compound and bound peptide from said sample;
   iv) dissociating the fucose-containing compound from the peptide; and
   v) optionally removing the peptide.

* * * * *